United States Patent [19]
Swanson

[11] 4,198,713
[45] Apr. 22, 1980

[54] PROTECTIVE MEMBER FOR IMPLANTABLE PROSTHESIS AND METHOD OF PROTECTING THE PROSTHESIS

[76] Inventor: Alfred B. Swanson, 2945 Bonnel, SE., Grand Rapids, Mich. 49506

[21] Appl. No.: 24,955

[22] Filed: Mar. 29, 1979

Related U.S. Application Data

[63] Continuation-in-part of Ser. No. 731,825, Oct. 12, 1976, Pat. No. 4,158,893.

[51] Int. Cl.² .............................................. A61F 1/24
[52] U.S. Cl. ..................................... 3/1.91; 128/92 C
[58] Field of Search ................................. 3/1.9–1.913; 128/92 C, 92 CA

[56] References Cited

U.S. PATENT DOCUMENTS

| 2,785,673 | 3/1957 | Anderson | 128/92 CA |
| 3,593,342 | 7/1971 | Niebauer | 3/1.91 |
| 3,605,123 | 9/1971 | Hahn | 128/92 C X |
| 3,681,786 | 8/1972 | Lynch | 3/1.91 |
| 3,744,061 | 7/1973 | Frost | 128/92 CA X |
| 3,745,590 | 7/1973 | Stubstad | 128/92 C X |
| 3,808,606 | 5/1974 | Tronzo | 3/1.9 |
| 3,816,854 | 6/1974 | Schlein | 128/92 C X |
| 3,818,513 | 6/1974 | Pillet | 128/92 C X |
| 3,820,167 | 6/1974 | Sivash | 3/1.912 |
| 3,848,272 | 0/1974 | Noiles | 3/1.913 |
| 3,875,594 | 4/1975 | Swanson | 3/1.91 |
| 3,879,767 | 4/1975 | Stubstad | 128/92 C X |
| 3,886,600 | 6/1975 | Kahn et al. | 128/92 C X |
| 3,924,274 | 12/1975 | Heimke et al. | 3/1.91 |
| 3,938,198 | 2/1976 | Kahn et al. | 3/1.912 |
| 3,992,725 | 11/1976 | Homsy | 3/1.9 X |

FOREIGN PATENT DOCUMENTS

| 2154338 | 5/1973 | Fed. Rep. of Germany | 3/1.911 |
| 2253338 | 5/1974 | Fed. Rep. of Germany | 3/1.9 |
| 2545821 | 4/1976 | Fed. Rep. of Germany | 3/1.911 |
| 1122634 | 5/1956 | France | 128/92 C |
| 1443470 | 7/1976 | United Kingdom | 3/1.9 |

Primary Examiner—Ronald L. Frinks
Attorney, Agent, or Firm—Price, Heneveld, Huizenga & Cooper

[57] ABSTRACT

A protectable device for preventing lacerations or tearing of a surgically implantable, flexible prosthesis by sharp bone edges includes a member having a generally curvilinear shield portion configured to conform to the prosthesis and a stem portion extending from the curvilinear shield portion and dimensioned to cover at least the top surface of a prosthesis intramedullary stem.

16 Claims, 4 Drawing Figures

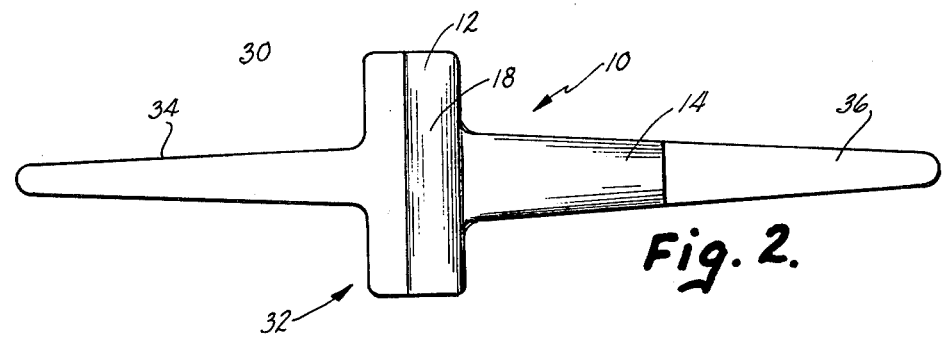
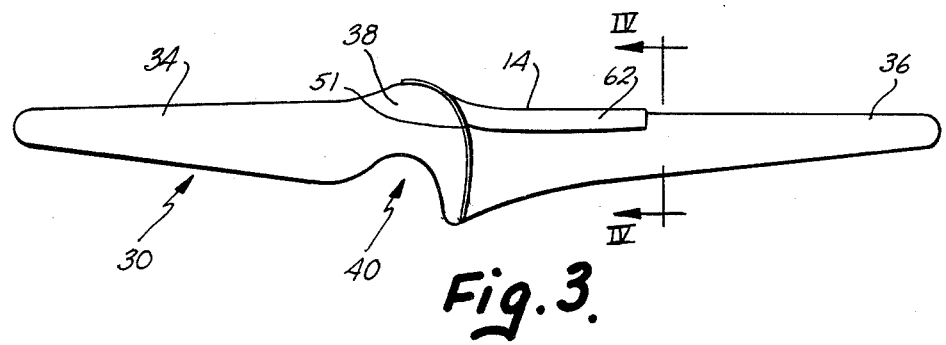
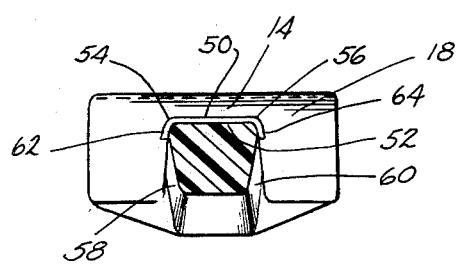
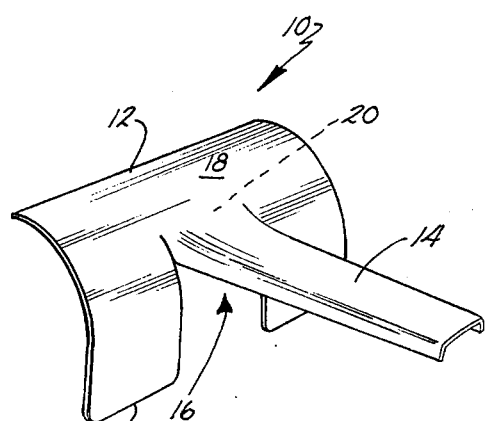

PROTECTIVE MEMBER FOR IMPLANTABLE PROSTHESIS AND METHOD OF PROTECTING THE PROSTHESIS

CROSS REFERENCE TO RELATED APPLICATION

This application is a continuation-in-part of co-pending application Ser. No. 731,825, filed Oct. 12, 1976, now U.S. Pat. No. 4,158,893.

BACKGROUND OF THE INVENTION

This invention relates to a unique protective device for and a method of protecting surgically implantable, flexible prosthetic joints from laceration or tearing caused by contact with the edges of adjacent bones and which serves to protect the bone from fracture.

Heretofore, various surgically implantable prosthetic devices have been proposed for replacing bone joints. Typically, the prosthesis includes a midsection or hinge portion and a pair of outwardly directed stem portions. The stem portions correspond generally to the dimensions of the intramedullary canals of the bones adjacent the joint and are implanted within the canals. Examples of such prosthetic joints may be found in Applicant's prior U.S. Pat. No. 3,875,594, issued Apr. 8, 1975, and entitled SURGICALLY IMPLANTABLE PROSTHETIC JOINT HAVING LOAD DISTRIBUTING FLEXIBLE HINGE.

As discussed in Applicant's co-pending application Ser. No. 731,825, filed Oct. 12, 1976, and entitled PROTECTIVE SLEEVE FOR IMPLANTABLE PROSTHESIS AND METHOD OF PROTECTING THE PROSTHESIS, experience in testing programs has indicated that the flex life of the flexible implants under consideration is essentially infinite unless a laceration or tear occurs on the surface. The joints are fabricated from flexible elastomeric, physiologically inert material such as silicone rubber. If a laceration or tear of the surface of the prosthesis should occur, tear propagation throughout the device will usually result, causing joint failure.

The problem of tear propagation is particularly acute with patients suffering from severe rheumatoid arthritis. Rheumatoid arthritis produces alterations of the bone and tendon balance of the joint which play an important role in the mechanism of the reconstructed joint. Further, the bones of these patients typically become thin and atrophied and the edges of the bones at the joint may become very sharp. Subluxation of the joint bones results in impingement of the sharp bone edges on the midsection of the implant and subsequent lacerations or tears. Further, the implant itself may exert sufficient pressure on the bone to result in fracture of the bone.

The protective device disclosed in the aforementioned application Ser. No. 731,825, the disclosure of which is hereby incorporated by reference, is an elongated, one-piece sleeve which surrounds the stem portion of the implant and defines a passage for receipt of the stem portion. The protective device is surgically implanted within an intramedullary canal of the bone adjacent the joint. The protective end portion extends from the canal in a flared or fluted manner and prevents impingement of the edges of the resected bone on the flexible joint.

SUMMARY OF THE INVENTION

In accordance with the present invention, an improved, unique protective device for preventing failure of a prosthesis and method of using same are provided. The protective device of the present invention is easier to manufacture at reduced costs and results in a simplification of the surgical procedure. Essentially, the device includes a member having a generally curvilinear shield portion configured to conform to the surface of the midsection of the prosthesis upon which a bone edge would impinge and a stem protecting portion extending from the curvilinear shield portion and dimensioned to cover a part of the top surface of the prosthesis stem. The member is fabricated from a material permitting reciprocation between the prosthesis stem and the member. The device is surgically implanted within one of the intramedullary canals of the bone adjacent the joint and prevents impingement of the bone edges and consequent laceration and tearing of the prosthesis.

The method of protecting a surgically implantable prosthesis in accordance with the present invention contemplates the forming of a member including a curvilinear shield portion and a stem portion and surgically implanting the member in an intramedullary canal prior to surgical implantation of the prosthesis.

BRIEF DESCRIPTION OF THE DRAWINGS

FIG. 1 is a perspective view of a protective device in accordance with the present invention;

FIG. 2 is a top, plan view of a flexible prosthesis and protective device in accordance with the present invention;

FIG. 3 is a side, elevational view thereof; and

FIG. 4 is a cross sectional view taken generally along line IV—IV.

DETAILED DESCRIPTION OF THE PREFERRED EMBODIMENT

The preferred embodiment of the protective device in accordance with the present invention is illustrated in the drawings and generally designated 10. As seen in FIG. 1, the protective device includes a one-piece member having a shield portion 12 and a stem portion 14. The shield portion 12 is generally curvilinear in vertical section. Shield 12 defines a generally rectangular aperture 16 opening through a lower edge 17 thereof. Stem portion 14 extends outwardly or rearwardly from the face 18 of the shield at an upper edge 20 of the aperture 16. Stem portion 14 tapers rearwardly from the shield. A prosthesis or implant protected by the device 10 is shown in FIGS. 2, 3 and 4. The implant is generally designated 30 and includes an enlarged midsection 32 and a pair of outwardly extending stems 34, 36. The prosthesis 30 includes a rounded, thickened section 38 along the upper or dorsal surface of the enlarged midsection 32 and a transverse trough or channel 40 formed in the lower or volar surface of the midsection. As best seen in FIG. 4, stems 34, 36 are preferably of generally rectangular shape in vertical cross section. The stems are configured for stability within the intramedullary canals of the bones. The cross sectional shape assists in preventing rotation of the prosthesis after implantation. The implants are fabricated from medical grade silicone rubber material. A more detailed description of the implant may be found in Applicant's prior U.S. Pat. No. 3,875,594 issued Apr. 8, 1975, and entitled SURGICALLY IMPLANTABLE PROSTHETIC JOINT HAVING LOAD DISTRIBUTING FLEXIBLE HINGE. To the extent necessary, the disclosure of this patent is hereby incorporated by reference.

During the implantation procedure, the natural joint is partially, surgically removed and the intramedullary canals of adjacent bone ends are prepared with a curette, broach or drill to receive the stem portions of the prosthesis. With certain patients, as previously stated, the edges of the bones adjacent the joint may become very sharp or ragged. These sharp edges have a tendency to impinge on the midsection 32 of the prosthesis resulting in lacerations or tearing of the upper surface and surfaces facing the bone end. Unless this impingement is prevented, fracture of the prosthetic joint may occur. Also, the thin bones are themselves subject to fracture.

As seen in FIGS. 2, 3 and 4, shield portion 12 of the protective device 10 is configured and dimensioned to completely cover the wear surface or outer surface 51 of the midsection 32 of the particular implant with which it is used. Shield 12 is smoothly configured to conform precisely to these surfaces of the particular implant. Stem portion 14 includes a generally flat or planar mid portion 50 which is dimensioned to completely cover the upper surface 52 of the stem 36. Portion 14 is rounded or curved downwardly adjacent the lateral edges 54, 56 so as to extend around and onto the side surfaces 58, 60 of prosthesis stem 36. Portion 14 is generally U-shaped in section and includes depending skirts 62, 64. Aperture 16, shield 12 and stem portion 14 define a passage which partially surrounds and through which the stem of the prosthesis extends. Stem portion 14 in cooperation with aperture 16 locates and positions the shield 12 relative to the prosthesis.

It is presently preferred that the prosthesis 30 and the protective device 10 be fabricated from materials which permit relative, sliding, reciprocating motion between the prosthesis and the protective device. The reciprocating motion reduces the chance of excessive stress being exerted on the bone structure by the prosthetic device after implantation. The stem portion 14 since it extends along the stem 36 and into the intramedullary canal of the bone reinforces the bone and serves as a weight or load bearing member. The protective device 10 must present a smooth surface to the bone structure and also to the implant. This is necessary to achieve the desired reciprocating motion. The implant always acts to retain the protective device within the intramedullary canal of the bone due to the implant's natural resilience. The pushing action of the prosthesis against the device 10 reduces the criticality of the fit between the device 10 and the bone intramedullary canal. The device may be loosely fitted within the bone as long as the implant biases the device into position. It is presently preferred that the implant be fabricated from highly polished, stainless steel. The implant is easily and readily manufactured by stamping with readily available processes and equipment.

The protective device may be configured to be used with any flexible hinge implant whether for replacement of a finger joint, a wrist joint or a toe joint. Although the present invention has been illustrated as being positioned on only one end of prosthesis 30, it can be positioned on either stem 34 or 36. Typically with replacement of a finger joint, it would be used at least at the distal end of the joint since the majority of the wear occurs at that area. The specific configuration of the protective device 10 may be varied somewhat from that illustrated. The primary consideration is that the major wear areas, that is the points where the bone impinges on the prosthesis, are covered.

The thickness of the protective device 10 would, of course, vary with the particular size implant employed and with the physical dimensions of the bones adjacent the restructured joint. The thickness of device 10 should be selected to reduce the dimensions of the intramedullary canal to provide a proper fit for the particular implant employed. Since the implants are provided in graduated sizes, the protective device 10 would also have to be provided in graduated sizes. The shield configuration would, of course, have to be varied for the particular configuration of the implant with which it is used. Further, it is presently preferred that the stem portion 14 have a length of approximately one third to one half the length of the stem portion of the implant. The primary consideration is to line or cover the exterior surface of the bone edge and the exterior surface of the implant so as to prevent direct contact between these surfaces. The major wear occurs along the upper edges of the bone and the upper surface of the enlarged midsection 32 of the prosthesis. The present invention due to its configuration covers these surfaces and reduces costs of manufacture. The material requirements are reduced and manufacture is simplified when compared with Applicant's prior protective device.

Device 10 is surgically implanted within the intramedullary canal of the bone prior to surgical implantation of the prosthesis. Shield 12 serves as a stop and prevents the device from being pushed into the bone canal during positioning of the prosthesis. This simplifies the surgical procedure. The invention eliminates or substantially reduces the occurrence of fracture of a silicone rubber or other flexible implant. This substantially increases the prognosis for restruction patients especially those suffering from severe rheumatoid arthritis at a reduced cost and with reduced surgical complexity than heretofore obtainable.

Those skilled in the art will readily appreciate the many advantages of the present invention. Those so skilled may also recognize that modifications may be made and it is expressly intended that the equivalent arrangements be covered unless the following claims by their wording, expressly state otherwise.

The embodiments of the invention in which an exclusive property or privilege is claimed are defined as follows.

1. A protective device for a flexible surgically implantable prosthesis used to replace bone joints, the prosthesis being of the type having a hinge portion and at least one outwardly directed stem; said device comprising:

a member including a generally curvilinear shield portion configured to conform to at least a portion of the outer surface of the hinge portion of the prosthesis and a stem portion extending from the curvilinear shield portion and dimensioned to cover at le\st a portion of the top surface of the prosthesis stem, said member being fabricated from a material permitting reciprocation between the prosthesis stem and the member.

2. A protective device as defined by claim 1 wherein said stem portion of said member tapers rearwardly along its length from the shield portion.

3. A protective device as defined by claim 2 wherein said shield portion defines an aperture opening through a lower edge thereof and dimensioned to permit the stem of the prosthesis to pass through the shield portion, said aperture having an upper edge and said stem portion of said member extending outwardly from the upper edge of the aperture.

4. A protective device as defined by claim 3 wherein said stem portion of said member is generally U-shaped in section to include depending skirts and said shield portion and stem portion define a passage through which the prosthesis stem extends.

5. A protective device as defined by claim 4 wherein said member is fabricated as a single piece from polished stainless steel.

6. In combination, a protective device and a surgically implantable flexible joint prosthesis, said prosthesis being of the type including a hinge portion and a stem extending outwardly from the hinge portion, the stem corresponding generally to the dimensions of the intramedullary canal of a bone adjacent the joint for insertion therein, said protective device comprising:

a one piece member defining a shield portion of curvilinear shape configured to conform and cover at least an upper wear surface of the prosthesis hinge portion against which the bone may impinge and a stem portion extending outwardly from the shield portion and along at least a portion of the upper surface of the prosthesis stem, said member and said prosthesis being sized relative to one another and being of such materials as to permit sliding, reciprocating movement of said prosthesis stem relative to said member subsequent to implantation of said prosthesis thereby protecting the bone from excessive stress.

7. The combination of claim 6 wherein said shield portion defines a generally rectangular aperture through which the stem of the prosthesis passes.

8. The combination of claim 7 wherein said member stem portion and said shield portion define a passage through which said prosthesis stem passes.

9. The combination of claim 8 wherein said stem portion of said member is generally U-shaped in section and includes downwardly angled lateral edge portions.

10. The combination of claim 9 wherein said stem portion of said member is integral with said shield at an upper edge of said aperture and tapers rearwardly along said prosthesis stem.

11. The combination of claim 10 wherein said member is fabricated from polished stainless steel.

12. A method of protecting a flexible surgically implantable prosthesis used in replacing bone joints and the like, from lacerations and tears caused by contact with the bone edges, the prosthesis being of the type including a midsection and at least one outwardly extending stem portion, the stem portion being insertable into the intramedullary canal of a bone adjacent the joint, comprising the steps of:

forming a member having a shield portion configured to conform to the wear surface of the prosthesis midsection adjacent the bone when implanted and a stem portion extending away from the shield portion and defining therewith a passage dimensioned for receipt of one of said stem portions;

surgically implanting said member stem protecting portion within said intramedullary canal prior to insertion of said stem portion and positioning said member so that the shield portion thereof is between the bone edge and said prosthesis midsection and covers said bone edge when said prosthesis is implanted.

13. A method as defined by claim 12 wherein said shield portion defines an aperture having an upper edge and said stem protecting portion is integral with said shield portion at said upper edge.

14. A method as defined by claim 13 wherein said aperture is generally rectangular in shape and opens through a lower edge of said shield portion.

15. A method as defined by claim 13 wherein step of forming said member includes forming the member from a material permitting sliding reciprocating movement of the prosthesis stem relative to said member.

16. A method as defined by claim 15 wherein said member is stamped as a single piece from polished stainless steel.

* * * * *

UNITED STATES PATENT AND TRADEMARK OFFICE
CERTIFICATE OF CORRECTION

PATENT NO. : 4,198,713
DATED : April 22, 1980
INVENTOR(S) : Alfred B. Swanson

It is certified that error appears in the above-identified patent and that said Letters Patent are hereby corrected as shown below:

Column 6, line 35:

After "wherein" insert --said--.

Signed and Sealed this

Fifteenth Day of July 1980

[SEAL]

Attest:

SIDNEY A. DIAMOND

Attesting Officer

Commissioner of Patents and Trademarks